United States Patent [19]

Nagai et al.

[11] 4,278,656

[45] Jul. 14, 1981

[54] COSMETIC COMPOSITION CONTAINING KOJIC ACID ESTER

[75] Inventors: Sumiyoshi Nagai; Tokio Izumi, both of Onojo, Japan

[73] Assignee: Sansho Pharmaceutical Co., Ltd., Onojo, Japan

[21] Appl. No.: 58,447

[22] Filed: Jul. 18, 1979

[30] Foreign Application Priority Data

Jun. 28, 1979 [JP] Japan .................................. 54-82257

[51] Int. Cl.$^3$ ....................... A61K 7/135; A61K 7/42; A61K 31/35
[52] U.S. Cl. ........................................ 424/62; 424/59; 424/283
[58] Field of Search ............................. 424/59, 283, 62

[56] References Cited

U.S. PATENT DOCUMENTS

| | | | |
|---|---|---|---|
| 2,865,930 | 12/1958 | Metivier et al. .................. | 424/283 X |
| 2,875,124 | 2/1959 | Gaertner et al. ..................... | 424/283 |
| 3,093,659 | 6/1963 | Bell et al. .......................... | 424/283 X |
| 3,852,444 | 12/1974 | D'Amico ............................. | 424/283 |

FOREIGN PATENT DOCUMENTS 53-03538  1/1978  Japan .
53-06432  1/1978  Japan .

OTHER PUBLICATIONS

Kato et al., Chem. Abs., 1967, vol. 67, pp. 89834d.
Abe et al., Chem. Abs., 1970, vol. 72, pp. 68486e.
Saruno et al., Chem. Abs. 1978, vol. 88; pp. 158291x.
Saruno et al., Chem. Abs., 1978, vol. 88, pp. 141505x.
Eiden, Chem. Abs., 1969, vol. 71, pp. 124115–124116.

*Primary Examiner*—Dale R. Ore
*Attorney, Agent, or Firm*—Armstrong, Nikaido, Marmelstein & Kubovcik

[57] ABSTRACT

A cosmetic composition containing a kojic acid ester with an aliphatic carboxylic acid, which is desirable for application to the skin. The kojic acid ester has an excellent effect of whitening the skin and an excellent antisuntan effect.

3 Claims, 3 Drawing Figures

COSMETIC COMPOSITION CONTAINING KOJIC ACID ESTER

BACKGROUND OF THE INVENTION

The present invention relates to a skin whitener cosmetic composition, and more particularly to a cosmetic composition having a skin whitening effect and an anti-suntan effect which contains an esterification product of kojic acid with an aliphatic carboxylic acid as an effective component.

There are known many cosmetic compositions designed to whiten the skin. Such skin whitener cosmetic compositions contain a peroxide such as hydrogen peroxide, zinc peroxide, magnesium peroxide, sodium peroxide, zinc perborate, magnesium perborate or sodium perborate. However, these peroxide compounds have problems in storability, physical and chemical stability and compatibility with other cosmetic ingredients and also the skin whitening effect is not sufficient. In recent years, skin whitener cosmetic compositions containing vitamin C, cysteine or colloidal sulphur were developed and have been availably employed, but the storability, stability and skin whitening effect are not still satisfactory.

SUMMARY OF THE INVENTION

Figure 1:
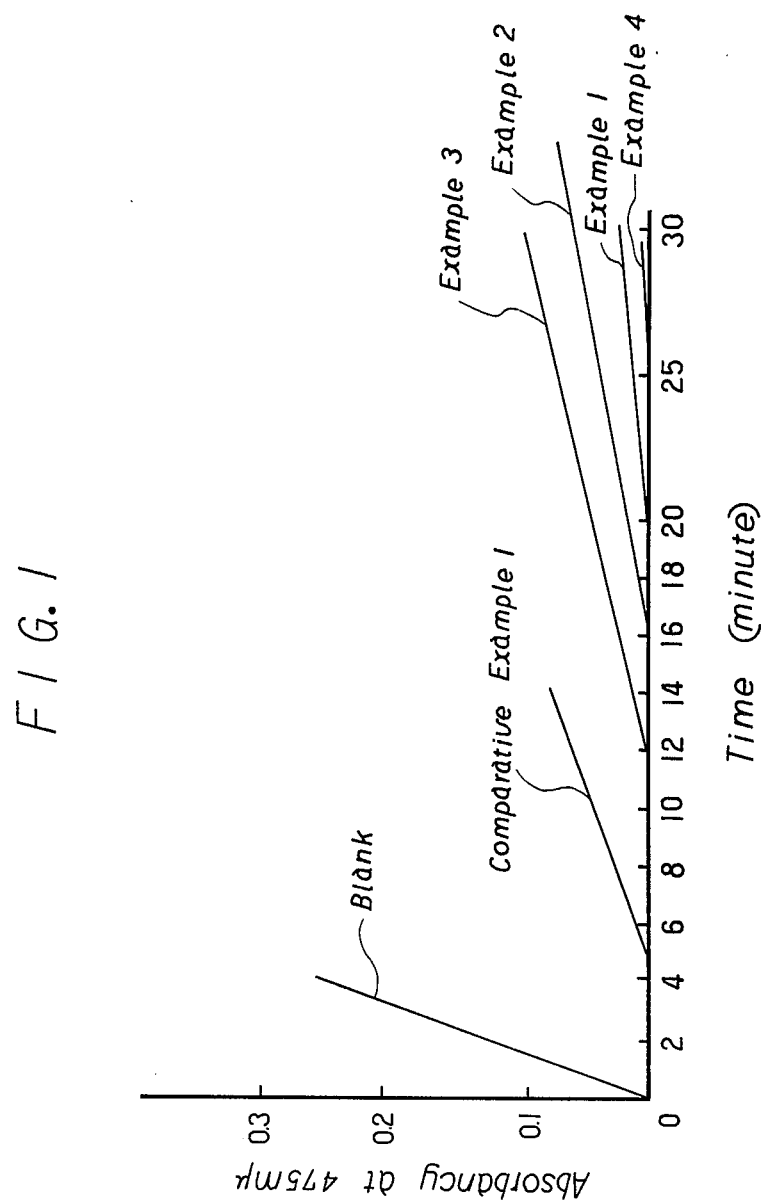
FIG. 1 is a graph showing the inhibitory effect on the activity of tyrosinase of cosmetic compositions according to the present invention.

It has now been found that an esterification product of kojic acid with an aliphatic carboxylic acid has an excellent property of inhibiting the activity of tyrosinase present in the human skin so as to inhibit the melanin formation and can produce excellent effects in whitening the skin and in anti-suntan, and also that the esterification product has an excellent stability to pH, heat and light.

According to the present invention, there is provided a skin whitener cosmetic composition containing an esterification product of kojic acid with an aliphatic carboxylic acid.

DETAILED DESCRIPTION

Esterification products of kojic acid with aliphatic carboxylic acids which are incorporated as an effective component into the skin whitener cosmetic composition of the present invention are compounds having the following formula:

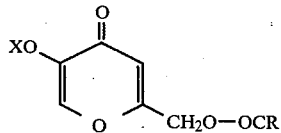

wherein X is hydrogen atom or a RCO-radical and RCO- is the residue of an aliphatic carboxylic acid.

These mono- and di-ester compounds are prepared in a known manner. For instance, the monoester compounds may be prepared by reacting kojic acid with an aliphatic carboxylic acid in the presence of a catalyst such as zinc chloride at an elevated temperature. The diester compounds may be prepared by adding an aliphatic acid halide to a pyridine solution of kojic acid and conducting the esterification reaction at a low temperature.

Although kojic acid itself has a high ability of inhibiting the activity of tyrosinase, the ability is further increased by converting kojic acid into the ester with an aliphatic carboxylic acid. In addition, the stability to pH, heat and light is increased, thus resulting in an excellent storability, and also the oil-solubility is increased and the ester can be more easily absorbed into the skin when it is incorporated in a cream. Thus the ester compounds according to the present invention have excellent skin whitening and anti-suntan effects.

The diester compounds according to the present invention have a particularly excellent stability and storability as compared with kojic acid and the monoester compounds. For instance, a vanishing cream containing 1% by weight of a diester compound according to the present invention shows no color change in storage at 45° C. for 4 weeks. On the other hand, a vanishing cream containing 1% by weight of kojic acid shows color change to deep yellowish brown and a vanishing cream containing 1% by weight of a monoester compound according to the present invention shows color change to light yellowish brown, in storage at 45° C. for 4 weeks.

Saturated aliphatic carboxylic acids, unsaturated aliphatic carboxylic acids, saturated aliphatic dicarboxylic acids, hydroxymonocarboxylic acids, hydroxydicarboxylic acids and hydroxytricarboxylic acids are employed as the aliphatic carboxylic acid in the present invention.

Examples of the saturated aliphatic carboxylic acid are acetic acid, propionic acid, butyric acid, n-valeric acid, iso-valeric acid, methylethylacetic acid, trimethylacetic acid, caproic acid, heptoic acid, caprylic acid, pelargonic acid, capric acid, undecylic acid, lauric acid, tridecylic acid, myristic acid, pentadecylic acid, palmitic acie, margaric acid, stearic acid, nonadecylic acid, arachic acid and lignoceric acid. Saturated aliphatic carboxylic acids having 3 to 20 carbon atoms, especially 8 to 20 carbon atoms are preferred, since the skin irritation due to the carboxylic acid is reduced even if the ester compound is decomposed. Saturated aliphatic carboxylic acids having 20 or more carbon atoms may be of course usable, but the use thereof increases the production cost, since they are not easily obtainable.

In addition to the saturated aliphatic carboxylic acids, there are employed in the present invention without particular limitation unsaturated aliphatic carboxylic acids such as linolic acid, linolenic acid, maleic acid, fumaric acid, oleic acid and arachidonic acid, saturated aliphatic dicarboxylic acids such as malonic acid, succinic acid and glutaric acid, hydroxymonocarboxylic acids such as lactic acid, hydroxydicarboxylic acids such as malic acid and tartaric acid, and hydroxytricarboxylic acids such as citric acid.

The skin whitener cosmetic composition of the present invention is prepared by incorporating the above-mentioned kojic acid ester into an adequate base cosmetic composition. The content of the kojic acid ester is selected from 0.01 to 10% by weight, preferably 1 to 5% by weight. When the content is lower than 0.01% by weight, sufficient skin whitening and anti-suntan effects cannot be obtained. On the other hand, even if the kojic acid ester is employed in an amount of more than 10% by weight, the effects cannot be increased in proportion to the amount.

The kojic acid ester according to the invention may be incorporated into various known cosmetic compositions in the form of a lotion, cream, pack, milk lotion etc. and, therefore, the cosmetic composition of the present invention may be prepared by admixing the kojic acid ester with suitable conventional cosmetic ingredients such as alcohols, animal and vegetable fats and oils, surface active agents, pectin, carboxymethyl cellulose, alginic acid salts, stabilizers, coloring agents, perfumes and others, and if desired, with heating or melting.

The followings are examples of formulating the kojic acid ester according to the invention, but it is to be understood that the present invention is not limited to these formulations.

| Formulation 1 (lotion) Ingredients | Parts by weight |
| --- | --- |
| Kojic acid dipalmitate | 1.00 |
| Aminoacetic acid | 0.20 |
| Pyridoxine hydrochloride | 0.05 |
| Zinc phenolsulfonate | 0.30 |
| Propylene glycol | 8.00 |
| Ethanol | 5.00 |
| Purified water | 86.35 |
| Perfume and antiseptic | slight |
| Formulation 2 (pack) | |
| Kojic acid dipalmitate | 4.00 |
| Aminoacetic acid | 0.20 |
| Zinc phenolsulfonate | 0.30 |
| Propylene glycol | 13.00 |
| Polyacrylic acid | 1.20 |
| Sodium oxide | 0.14 |
| Ethanol | 2.50 |
| Titanium dioxide | 0.02 |
| Purified water | 82.54 |
| Perfume and antiseptic | slight |
| Formulation 3 (pack) | |
| Kojic acid dibutyrate | 1.50 |
| Polyvinyl alcohol | 15.00 |
| Polyvinylpyrrolidone | 4.00 |
| Propylene glycol | 6.00 |
| Ethanol | 10.00 |
| Purified water | 69.70 |
| Perfume and antiseptic | slight |
| Formulation 4 (milk lotion) | |
| Kojic acid dipalmitate | 4.00 |
| Stearic acid | 2.00 |
| Cetanol | 0.50 |
| Lanolin | 2.00 |
| Oleyl oleate | 2.00 |
| Squalane | 3.00 |
| Liquid paraffin | 8.00 |
| Emulsifier | 2.60 |
| Triethanolamine | 1.00 |
| Propylene glycol | 4.00 |
| Purified water | 74.90 |
| Perfume, antioxidant and antiseptic | slight |
| Formulation 5 (vanishing cream) | |
| Kojic acid dioleate | 4.00 |
| Microcrystalline stearic acid | 8.00 |
| Beeswax | 5.00 |
| Cetanol | 3.00 |
| Lanolin | 2.00 |
| Isopropyl myristate | 6.00 |
| Liquid paraffin | 7.00 |
| Olive oil | 2.00 |
| Emulsifier | 5.50 |
| Triethanolamine | 0.60 |
| Propylene glycol | 3.00 |
| Purified water | 57.70 |
| Perfume, antioxidant and antiseptic | slight |

-continued

| Formulation 1 (lotion) Ingredients | Parts by weight |
| --- | --- |
| Formulation 6 (cold cream) | |
| Kojic acid distearate | 4.00 |
| Beeswax | 10.00 |
| Ceresine | 7.00 |
| White vaseline | 3.00 |
| Lanolin | 3.00 |
| Isopropyl myristate | 3.00 |
| Squalane | 4.00 |
| Liquid paraffin | 40.00 |
| Polyoxyethylene cetyl ether | 2.70 |
| Emulsifier | 2.30 |
| Propylene glycol | 2.00 |
| Purified water | 23.00 |
| Perfume, antioxidant and antiseptic | slight |

The present invention is more particularly described and explained by means of the following Examples, in which all % and parts are by weight unless otherwise noted. In order to illustrate the preparation of the kojic acid ester with an aliphatic carboxylic acid, the following Reference Examples are also presented.

REFERENCE EXAMPLE 1

A flat bottom flask was charged with a culture medium of pH 4 containing 5% of sucrose, 0.03% of potassium dihydrogenphosphate, 0.01% of magnesium sulfate, 0.01% of calcium chloride, 0.001% of ferric chloride, 0.001% of sodium chloride and 0.5% of peptone in an amount of half the volume of the flask. After subjecting it to autoclaved sterilization under a pressure of 1 kg./cm.$^2$ for 15 minutes, Aspergillus albus obtained from Utsunomiya University was inoculated into the medium and was statically cultured at 28° C. for 10 days. After the culture, mycelial mat was removed from the culture liquor and the culture liquor was then filtered to give a fermented liquor containing 2.5% of kojic acid.

To 1,000 ml. of the fermented liquor was added 400 ml. of a 5% aqueous solution of cupric acetate, the mixture was then centrifuged at 3,000 r.p.m. for 20 minutes to give 150 g. of a precipitate. The precipitate was suspended into 1,500 ml. of water, and hydrogen sulfide was sufficiently passed through the suspension to give a precipitate of cupric sulfide. After removing cupric sulfide by filtration, the obtained filtrate was concentrated at 50° C. under a reduced pressure to give 500 ml. of a concentrated liquor. The concentrated liquor was then extracted with three 2,000 ml. portions of ethyl acetate, and the extract was concentrated at 50° C. under a reduced pressure to give 25 g. of crude crystal of kojic acid. The crude crystal was recrystallized from 2,000 ml. of ethyl acetate to give 20 g. of kojic acid.

To 28.5 g. (0.1 mole) of stearic acid was added 4.1 g. (0.03 mole) of zinc chloride, and the mixture was heated at 140° C. for 30 minutes and thereto was gradually added 4.3 g. (0.03 mole) of kojic acid with agitation. The mixture was further maintained at 140° C. for 2.5 hours with agitation. After allowing to stand overnight at room temperature, the mixture was washed with 300 ml. of water and was extracted with three 2,000 ml. portions of ether. The resulting ether extract was neutralized with sodium hydrogencarbonate, and was then concentrated at 30° C. under a reduced pressure to give a crude crystalline product. The crude product was then recrystallized from 300 ml. of ether to give 13 g. of a purified esterification product of kojic acid and stearic acid, i.e. monoester of the following formula:

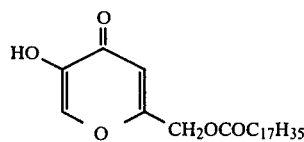

REFERENCE EXAMPLE 2

The procedures of Reference Example 1 were repeated except that 28.2 g. (0.1 mole) of oleic acid was employed instead of stearic acid, to give 12.8 g. of an esterification product of kojic acid and oleic acid.

REFERENCE EXAMPLES 3 AND 4

The procedures of Reference Example 1 were repeated except that 22.8 g. (0.1 mole) of myristic acid or 14.4 g. (0.1 mole) of caprylic acid and a commercially available kojic acid made by Sigma Chemical Corp. were employed instead of stearic acid and kojic acid prepared in Reference Example 1, to give 12 g. of an esterification product of kojic acid and myristic acid and 7.5 g. of an esterification product of kojic acid and caprylic acid, respectively.

There are shown in Table 1 the melting point of the kojic acid monoesters obtained in Reference Examples 1 to 4 and the results of the ferric chloride test which was conducted by measuring the absorbancy at 500 m$\mu$ of a water-ethanol (9:1 by weight) solution containing 0.5 micromole of the kojic acid monoester per ml. to confirm that the acylation of kojic acid with a carboxylic acid took place at the position of methylol group.

TABLE 1

| Acid component | Melting point (°C.) | Ferric chloride test (absorbancy at 500 m$\mu$) |
| --- | --- | --- |
| Ref. Ex. 1 Stearic acid | 95 to 97 | 0.645 |
| Ref. Ex. 2 Oleic acid | 21.5 to 23.5 | 0.644 |
| Ref. Ex. 3 Myristic acid | 84 to 86 | 0.644 |
| Ref. Ex. 4 Caprylic acid | 74.5 to 75 | 0.644 |
| Blank (Kojic acid alone) | 153.5 to 154.5 | 0.645 |

REFERENCE EXAMPLE 5

In 2 ml. of pyridine was dissolved 100 mg. (0.704 millimole) of kojic acid, and thereto was added dropwise 446.4 mg. (1.624 millimoles) of palmityl chloride over 30 minutes at room temperature with agitation. The resulting mixture was allowed to stand overnight at room temperature. The obtained yellow reaction mixture was poured into 50 ml. of ice water, and the resulting white precipitate was separated by filtration, washed with water and dried to give 643 mg. of a crude product having melting point of 72° to 86° C. The crude product was recrystallized from acetone to give 412 mg. of white glossy powder having a melting point of 91° to 92° C. The yield was 94.3%. The further recrystallized product from acetone had a melting point of 92° to 93° C.

By thin layer chromatography (solvent: chloroform/ethanol=9/1 or benzene/ethyl acetate=9/1, plate: Silica-gel GF254 made by Merck & Co., Inc.), it was confirmed that the obtained product was kojic acid dipalmitate shown by the following formula:

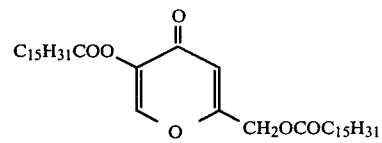

The results of the elemental analysis and infrared spectrophotometry conducted for identification were as follows:

Elemental analysis: Calculated for $C_{38}H_{66}O_6$: C 73.66%; H 11.32%; Found: C 73.74%; H 10.75%

Infrared absorption spectrum ($\nu_{max}^{Nujol}$ cm$^{-1}$):

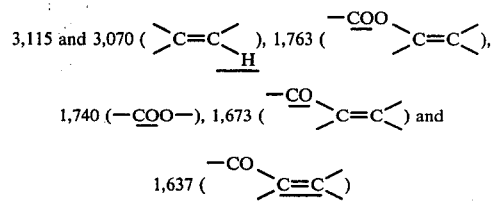

REFERENCE EXAMPLE 6

In 1 ml. of pyridine was dissolved 100 mg. (0.704 millimole) of kojic acid, and 174.9 mg. (1.641 millimoles) of butyryl chloride was added dropwise with agitation to the pyridine solution with ice cooling. After 30 minutes, an ice-water bath was removed to raise the mixture to room temperature. After agitating the mixture for 4 hours at room temperature, the resulting yellow reaction mixture was poured into ice water. The resulting colorless oily material was extracted with benzene. The benzene extract was then washed with a 10% aqueous solution of $Na_2CO_3$ and a saturated aqueous solution of $Cu_2SO_4$ in that order, was dried with anhydrous magnesium sulfate and was filtered. From the filtrate, benzene was distilled away under a reduced pressure to give 190 mg. of a colorless oily material (yield: 95.7%). Colorless needle-like crystal having a melting point of 31° to 38° C. was obtained by cooling the oily material. The thus obtained crude product was recrystallized from methanol to give colorless needle-like crystal having a melting point of 41.5° C.

By the silica-gel thin layer chromatography, elemental analysis and infrared spectrophotometry, it was confirmed that the obtained colorless needle-like crystal was kojic acid dibutyrate.

The results of elemental analysis and infrared spectrophotometry are as follows:

Elemental analysis: Calculated for $C_{14}H_{18}O_6$: C 59.50%, H 6.52%; Found: C 59.56%, H 6.43%

Infrared absorption spectrum ($\nu_{max}^{Nujol}$ cm$^{-1}$):

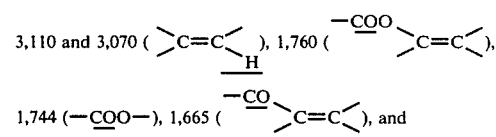

-continued 1,632 ( 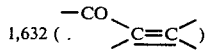 )

REFERENCE EXAMPLE 7

In 2 ml. of pyridine was dissolved 100 mg. (0.704 millimole) of kojic acid, and 448.7 mg. (1.491 millimoles) of oleyl chloride was added dropwise with agitation to the pyridine solution with cooling by ice over one hour. The mixture was further agitated for 2 hours with ice cooling, and was then allowed to stand overnight at room temperature. The resulting yellow reaction mixture was poured into 50 ml. of ice water, and the resulting white precipitate was separated by filtration, washed with water and dried to give 566.8 mg. of a crude product having a melting point of 33° to 40° C. The crude product was recrystallized from methanol to give 420 mg. of colorless needle-like crystal having a melting point of 38° to 40° C. The yield was 89%.

By the silica-gel thin layer chromatography, elemental analysis and infrared spectrophotometry, it was confirmed that the obtained needle-like crystal was kojic acid dioleate.

The results of elemental analysis and infrared spectrophotometry are as follows:

Elemental analysis: Calculated for $C_{42}H_{70}O_6$: C 74.66%; H 11.01%; Found: C 75.18%; H 10.52%

Infrared absorption spectrum ($v_{max}^{Nujol}$ cm$^{-1}$):

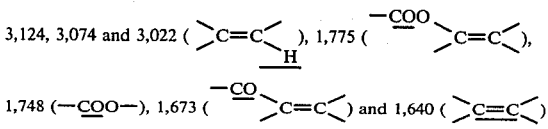

REFERENCE EXAMPLE 8

In 5 ml. of pyridine was dissolved 100 mg. (0.704 millimole) of kojic acid, and 449.8 mg. (1.484 millimoles) of stearyl chloride was added dropwise with agitation to the pyridine solution at room temperature over 20 minutes. After allowing the mixture to stand overnight at room temperature, the resulting yellow reaction mixture was poured into 50 ml. of ice water, and the resulting white precipitate was separated by filtration, washed with water and dried to give 534.8 mg. of a crude product having a melting point of 86° to 88° C. The crude product was recrystallized from ethyl acetate to give 434 mg. of white glossy powder having a melting point of 88° to 91° C. The yield was 91.4%. White glossy powder purified by further recrystallization had a melting point of 90° to 91° C.

By the silica-gel thin layer chromatography, elemental analysis and infrared spectrophotometry, it was confirmed that the product was kojic acid distearate.

The results of elemental analysis and infrared spectrophotometry are as follows:

Elemental analysis: Calculated for $C_{42}H_{74}O_6$: C 74.52%; H 11.55%; Found: C 74.73%; H 11.05%

Infrared absorption spectrum ($v_{max}^{Nujol}$ cm$^{-1}$):

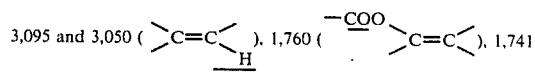

-continued

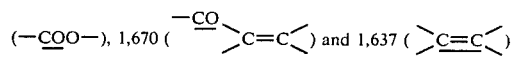

EXAMPLES 1 TO 4 AND COMPARATIVE EXAMPLE 1

There were prepared 1.0% liniments by dissolving in ethanol the monoester with stearic acid obtained in Reference Example 1 (Example 1), the monoester with oleic acid obtained in Reference Example 2 (Example 2), the monoester with myristic acid obtained in Reference Example 3 (Example 3), the monoester with caprylic acid obtained in Reference Example 4 (Example 4) or a pure kojic acid (Comparative Example 1).

The inhibitory effect on the activity of tyrosinase of the prepared liniments was examined as follows:

A test tube was charged with 1 ml. of an aqueous solution of L-tyrosine (0.3 mg./ml.), 1 ml. of McIlvaine's buffer solution of pH 6.8 and 0.9 ml. of a liniment, and was placed in a constant temperature water bath at 37° C. After incubation for 10 minutes, 0.1 ml. of an aqueous solution of tyrosinase (1 mg./ml.) was added to the tube and agitated, and the absorbancy was measured at 475 mμ with the lapse of time by employing a spectrophotometer.

As a blank test, the measurement of absorbancy was conducted in the same manner by employing water instead of the liniment.

The results are shown in FIG. 1.

It is understood from FIG. 1 that the liniments of Examples 1 to 4 have an excellent effect of inhibiting the activity of tyrosinase as compared with the liniment containing kojic acid of Comparative Example 1.

EXAMPLES 5 TO 8 AND COMPARATIVE EXAMPLE 2

There were prepared 1% liniments by dissolving in 100 ml. of a water-ethanol solvent (1:1 by weight) 1.0 g. of the monoester with stearic acid (Example 5), the monoester with oleic acid (Example 6), the monoester with myristic acid (Example 7), the monoester with caprylic acid (Example 8), which were obtained in Reference Examples 1 to 4 respectively, or a pure kojic acid (Comparative Example 2).

The stability to pH and heat was examined as follows.

After adjusting the liniments to pH 10.0 with sodium hydroxide, the liniments were maintained at 50° C. and the degree of coloration was observed by measuring the absorbancy at 420 mμ with the lapse of time employing a spectrophotometer.

Figure 2:
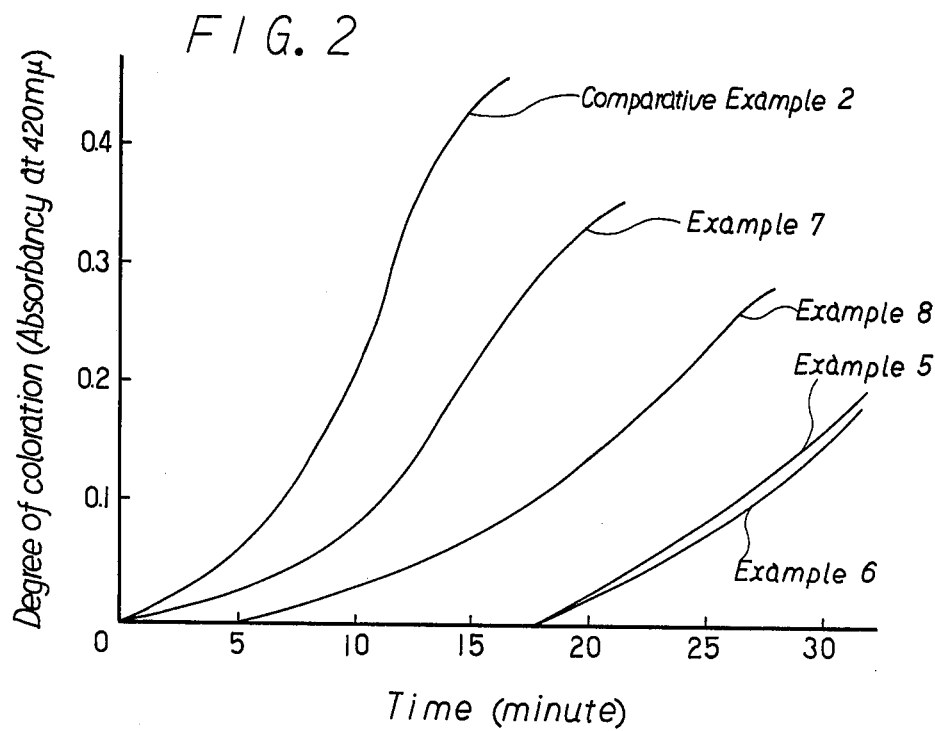
FIG. 2 is a graph showing the stability to pH and heat of cosmetic compositions according to the present invention.

The results are shown in FIG. 2.

It is understood from FIG. 2 that the liniments of Examples 5 to 8 have an excellent stability to pH and heat as compared with the liniment containing kojic acid of Comparative Example 2.

The stability to light was also examined as follows.

The liniments were exposed to ultraviolet ray of 270 mμ, and the degree of coloration was observed by measuring the absorbancy at 420 mμ with the lapse of time employing a spectrophotometer.

Figure 3:
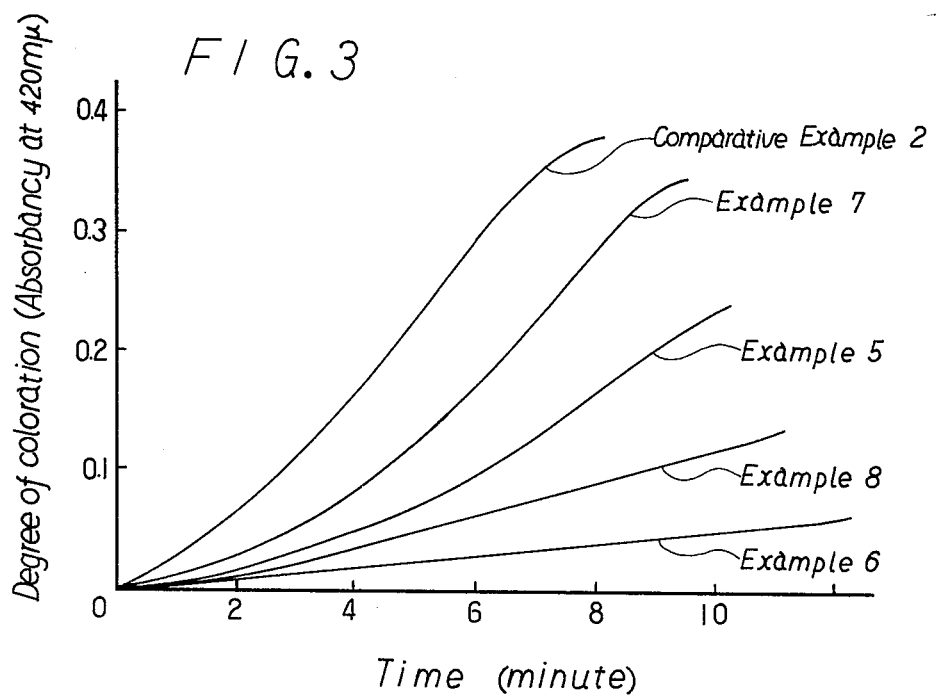
FIG. 3 is a graph showing the stability to light of cosmetic compositions according to the present invention.

The results are shown in FIG. 3.

It is understood from FIG. 3 that the liniments of Examples 5 to 8 have an excellent stability to light as compared with the liniment containing kojic acid of Comparative Example 2.

EXAMPLE 9

By employing the kojic acid monoester with myristic acid obtained in Reference Example 3, a vanishing cream was formulated from the ingredients shown in Table 2.

TABLE 2

| Ingredients | parts by weight |
| --- | --- |
| Stearic acid | 8 |
| Cetanol | 3 |
| Beeswax | 5 |
| Lanolin | 2 |
| Isopropyl myristate | 6 |
| Olive oil | 2 |
| Liquid paraffin | 7 |
| Sorbitan monostearate | 5.5 |
| Kojic acid monoester | 8 |
| Triethanolamine | 0.6 |
| Propylene glycol | 3 |
| Purified water | 49.9 |
| Antioxidant and antiseptic | proper amount |
| Perfume | proper amount |

One gram of the thus prepared vanishing cream was uniformly applied to 2 cm.$^2$ of arm of 40 panel persons, and 1, 2 and 3 MED (minimum erythema dose) of ultraviolet rays of 270 m$\mu$ and 340 m$\mu$ were applied to the applied surface. No erythema was observed on all panel persons.

EXAMPLE 10

By employing the kojic acid dipalmitate obtained in Reference Example 5, a vanishing cream was formulated from the ingredients shown in Table 3.

TABLE 3

| Ingredients | parts by weight |
| --- | --- |
| Kojic acid dipalmitate | 4 |
| Stearic acid | 8 |
| Cetanol | 3 |
| Beeswax | 5 |
| Lanolin | 2 |
| Isopropyl myristate | 6 |
| Olive oil | 2 |
| Liquid paraffin | 7 |
| Sorbitan monostearate | 5.5 |
| Triethanolamine | 0.6 |
| Propylene glycol | 3 |
| Purified water | 49.9 |
| Antioxidant and antiseptic | proper amount |
| Perfume | proper amount |

The inhibitory effect on the activity of tyrosinase of the thus prepared vanishing cream was examined as follows.

The vanishing cream was applied once daily to 82 women of pigmentation disease (20 to 45 years old) for 3 months, and the following result was obtained.

Complete cure: 25 persons
Improvement: 41 persons
No change: 16 persons

Vanishing creams were also prepared by employing the kojic acid diesters obtained in Reference Examples 6 to 8 in the same manner as above, and the inhibitory effect on the activity of tyrosinase was examined. The similar results to the above were obtained on all vanishing creams.

From these test results, it was confirmed that the cosmetic composition of the present invention was effective on about 80% of pigmentation diseases and had an excellent effect of inhibiting the activity of tyrosinase.

What we claim is:

1. A method of whitening human skin comprising the steps of applying to said skin an effective skin whitening amount of an aqueous composition in the form of a lotion, cream, pack, or milk lotion comprising a diester of kojic acid having the formula

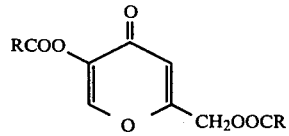

wherein R is an aliphatic group containing from 3 to 20 carbon atoms, said diester comprising from 0.01 to 10% by weight of said aqueous cosmetic composition and allowing said composition to whiten said skin.

2. A method of whitening human skin as in claim 1 wherein said content of said esterification product is from 1 to 5% by weight.

3. A method of whitening human skin as in claim 2, wherein said aliphatic carboxylic acid is a member selected from the group consisting of a saturated aliphatic carboxylic acid, an unsaturated aliphatic carboxylic acid, a saturated aliphatic dicarboxylic acid, hydroxymonocarboxylic acid, hydroxydicarboxylic acid and hydroxytriacarboxylic acid.

* * * * *